(12) United States Patent
Cougoulic

(10) Patent No.: US 7,902,270 B2
(45) Date of Patent: Mar. 8, 2011

(54) MEDICAL OR VETERINARY MATERIAL, METHOD FOR THE PRODUCTION AND USE THEREOF

(75) Inventor: Jean-Pierre Cougoulic, Pornichet (FR)

(73) Assignee: Catherine Cadorel, La Baule (FR)

( * ) Notice: Subject to any disclaimer, the term of this patent is extended or adjusted under 35 U.S.C. 154(b) by 420 days.

(21) Appl. No.: 10/540,756

(22) PCT Filed: Dec. 23, 2003

(86) PCT No.: PCT/FR03/50208
§ 371 (c)(1), (2), (4) Date: Jun. 24, 2005

(87) PCT Pub. No.: WO2004/058319
PCT Pub. Date: Jul. 15, 2004

(65) Prior Publication Data
US 2006/0052479 A1 Mar. 9, 2006

(30) Foreign Application Priority Data
Dec. 24, 2002 (FR) .................................... 02 16627

(51) Int. Cl.
*A61F 2/28* (2006.01)
*A61F 2/02* (2006.01)
*A61L 27/46* (2006.01)
*C08K 3/32* (2006.01)
*B29C 45/00* (2006.01)
*B08B 3/12* (2006.01)
*B08B 3/08* (2006.01)
*B08B 3/04* (2006.01)

(52) U.S. Cl. .......... 523/113; 523/114; 523/115; 524/417; 623/23.5; 623/23.51; 134/21; 134/26; 134/27; 134/28; 134/29; 134/36; 427/2.27; 264/328.18

(58) Field of Classification Search .................. 523/113, 523/115, 114; 528/355, 356; 524/417; 264/328.18; 623/23.5, 23.51; 134/21, 26, 27, 28, 29, 134/36; 427/2.27
See application file for complete search history.

(56) References Cited

U.S. PATENT DOCUMENTS

| | | | | |
|---|---|---|---|---|
| 5,456,723 A | * | 10/1995 | Steinemann et al. | 623/23.53 |
| 5,509,968 A | * | 4/1996 | Carr | 134/1 |
| 5,716,454 A | * | 2/1998 | Carr | 134/1 |
| 5,797,871 A | * | 8/1998 | Wolfinbarger, Jr. | 604/500 |
| 5,872,159 A | | 2/1999 | Cougoulic | |
| 6,207,218 B1 | * | 3/2001 | Layrolle et al. | 427/2.27 |
| 6,482,584 B1 | * | 11/2002 | Mills et al. | 435/1.1 |
| 2002/0111694 A1 | * | 8/2002 | Ellingsen et al. | 623/23.57 |
| 2004/0037735 A1 | * | 2/2004 | DePaula et al. | 422/20 |
| 2004/0199261 A1 | * | 10/2004 | Jones | 623/23.5 |
| 2005/0008620 A1 | * | 1/2005 | Shimp et al. | 424/93.7 |
| 2005/0170070 A1 | * | 8/2005 | Layrolle et al. | 427/2.1 |

* cited by examiner

Primary Examiner — Mark Eashoo
Assistant Examiner — Michael Pepitone
(74) Attorney, Agent, or Firm — Young & Thompson

(57) ABSTRACT

A material can be molded into part made of a biocompatible binder containing one or several compounds for adding calcium and phosphorus It has been subjected to a surface pickling operation intended to ensure surface application and hence surface access of the elements added to the binder, in particular calcium and phosphorus. This material may advantageously be used for the realization of endo-bone implants or bone prostheses.

4 Claims, No Drawings

MEDICAL OR VETERINARY MATERIAL, METHOD FOR THE PRODUCTION AND USE THEREOF

This application is a 35 U.S.C §371 U.S. National Stage Application of International Application No. PCT/FR03/50208, filed on Dec. 23, 2003, claiming priority of France Application No. 02/16627, filed Dec. 24, 2002.

BACKGROUND OF THE INVENTION

1. Field of the Invention

The present invention refers to an original material which may be used in the medical or veterinary filed, in particular but not exclusively for the realisation of endo-bone implants, in particular dental implants, of for the realisation of bone prostheses. The invention also refers to the method of production of such material, as well as the applications thereof.

2. Description of the Related Art

Numerous types of materials, metal or plastic materials are used in the medical or veterinary field for replacing biological structures (bone in particular) or for fastening functional organs (dental implants or others . . . ).

The material is selected in relation to its intrinsic structural characteristics and also in relation to its biocompatibility in terms of tolerance or, even better, in terms of biological acceptance.

The document FR-A-2 72 694 describes a moulded material for the realisation of endo-bone implants or of bone prostheses, made of thermoplastic polymer (in particular poly (etheretherketon), also called PEEK) comprising calcium hydroxyapatite, tricalcic phosphate, orthophosphoric acid and a $TiO_2$-type zeolite.

In spite of the encouraging results obtained with this type of material, it appears that the results in terms of biological integration are not quite satisfactory.

SUMMARY OF THE INVENTION

The present invention offers a new material derived from that described in the document aforementioned FR-A-2 722 694, which combines good overall mechanical qualities and very good biocompatibility in terms of biological acceptance, enabling thereby efficient use in the medical field as well as in the veterinary field.

DETAILED DESCRIPTION OF THE PREFERRED EMBODIMENTS

The material corresponding is in the form of a moulded part made of a biocompatible binder containing one or several compounds for adding calcium and phosphorus, which moulded part has been subjected to surface pickling operation.

Such pickling ensures surface application and hence surface access of the elements added to the binder, in particular calcium and phosphorus; this enables to create or at least to promote the creation of ionic links between such added elements and the surrounding chemical elements, mineral or organic elements, after biological implantation of the material part. And in case of resorbable added elements present, once such elements have disappeared, the tissues, the biological cells or the surrounding chemical elements may find a place for integration in the material.

This particularity enables to improve the adherence and the cell colonisation to ensure good biological graft-type acceptance and good biocompatibility of the implant.

The biocompatible binder is selected in relation to its physical characteristics after shaping in particular by an injection-moulding operation. By way of example, a thermoplastic polymer such as poly(etheretherketon), ketone polyether, amide block polyether, polytétrafluoréthylène or still polyimide may be used; a natural polymer, in particular such as cellulose, may also be utilised. Such polymer can be resorbable or not.

Because of its high Young's modulus and its interesting structural characteristics, close to those of the bone, poly (etheretherketon) (PEEK) is used preferably. PEEK is a semi-crystalline polymer made of an aromatic linear chain based on the repetition of the following units:

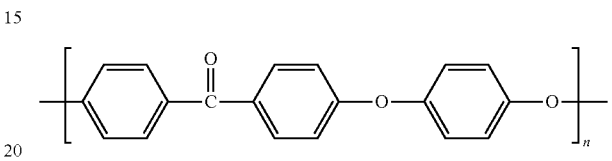

The characteristics of this polymer are expanded on in the commercial leaflet published in 1992 by ICI MATERIALS: <<Victrex PEEK, the high temperature engineering thermoplastic-properties and processing>>.

The additions of calcium and phosphorus are composed advantageously of calcium phosphates derived form example from tricalcic phosphate ($Ca_3(PO_4)_2$), dicalcic or monetite phosphate ($CaHPO_4$), with stoichiometric formulation (($Ca_5(PO_4)_3$ OH) or ($Ca_{10}(PO_4)_6H20$)), with stoichiometric formulation or not, or of products containing said elements.

The presence of calcium phosphates enables the material to approximate the natural composition of the bone in order to enhance the biocompatibility thereof. Products containing calcium phosphates, which are at least partially resorbable, are used preferably.

In particular, calcium hydroxyapatite is a component that can be found in the bone. It can be utilized advantageously in its non-stoichiometric form, since it is then slightly resorbable, which is interesting for cellular integration.

Dicalcic or tricalcic phosphate is advantageously cheap and one of the basic biological components for the formation of calcium hydroxyapatite; it is also resorbable and has also a healing function.

These various additions of calcium phosphates may also be used as mixtures.

Besides the addition of calcium phosphates, the moulded material according to the invention may contain orthophosphoric acid ($H_3(PO_4)$). Natural orthophosphoric acid is prescribed as a calcium fixative and as an acidifier; it is also a fundamental component of the nucleotides which as the basic units of nucleic acids, which partake of the constitution of the nucleus of living cells.

Moreover, the material according to the invention is advantageously laden with one or several compounds enabling to create or promote the electrostatic links with the surrounding medium. This(these) charge(s) may be selected among zeolites and/or certain oxides: using ceramics such as titanium dioxide ($TiO_2$), zirconium dioxide ($ZrO_2$), aluminium oxide ($Al_2O_3$) or silicium dioxide ($SiO_2$) may be contemplated.

The charges in question are electrostatic compounds which allow ionic bonding function; they have moreover high molar mass and they contribute to improve the radio-opacity of the material.

The material according to the invention is shaped by moulding, injection or extrusion moulding, of a homogeneous mixture of constituents. The material and the moulding conditions are suited to this mixture, and in particular the nature of the binder used.

To keep a mouldable material with sufficient handling and resistance, the polymer binder represents at least 65%, and preferably 65% to 90%, in weight of the finished material.

On the other hand, to add sufficient quantity of chemical elements intended to promote the biological integration, the complementary components (tricalcic phosphate and/or dicalcic phosphate and/or calcium hydroxyapatite, possibly associated with at least one compound of zeolite or oxide type for example, intended to improve electrostaticity and radio-opacity, and with orthophosphoric acid) represent between 10 and 35% in weight of the finished material.

A good compromise, in particular in terms of mechanical characteristics corresponds substantially to 80% in weight of polymer binder and 20% in weight of complementary component(s).

The invention also refers to the method of production of such material. The corresponding method comprises:—mixing homogeneously a mouldable binder biocompatible with one or several components for adding calcium and phosphorus,—subjecting the mixture thus obtained to a moulding operation,—performing one or several surface pickling and decontamination operations of the moulded part,—conditioning aseptically said decontaminated part.

The surface pickling operation is advantageously carried out by dint of at least one bath in a solution, in particular a pickling product, subjected to ultrasounds.

Preferably, the surface pickling and decontamination operations consist in passing the moulded part in successive baths of hydrochloric or sulphuric acid, acetone, hydrogen peroxide, sodium hypochloride and disinfectant product(s), submitted to ultrasounds, separated by operations consisting in water rinsing or passing in water baths submitted to ultrasounds.

EXAMPLES

Basic mixtures are prepared out of poly(etheretherketon) (PEEK), tricalcic phosphate ($Ca_3(PO_4)_2$), and titanium dioxide ($TiO_2$).

The PEEK is in the form of a powder or of granules (size: approx. 100 microns), available from Victrex Europa GmbH, Hauptstr. 11 D-65719 HOFHEIM—Germany.

Tricalcic phosphate is available in the form of a powder (grain size close to 200 microns); it is for instance marketed by Coopération Pharmaceutique Française, 77020 MELUN—France.

Titanium oxide is also available in the form of a powder distributed by Coopération Pharmaceutique Française, 77020 MELUN—France.

a) Proportions
Some possible examples of compositions are specified below:

| Mixture 1 (10% charges) | | Mixture 2 (20% charges) | |
|---|---|---|---|
| PEEK | 90% in weight | PEEK | 80% in weight |
| $Ca_3(PO_4)_2$ | 5% in weight | $Ca_3(PO_4)_2$ | 10% in weight |
| $TiO_2$ | 5% in weight | $TiO_2$ | 10% in weight |
| Mixture 3 (30% charges) | | Mixture 4 | |
| PEEK | 70% in weight | PEEK | 65% in weight |
| $Ca_3(PO_4)_2$ | 15% in weight | $Ca_3(PO_4)_2$ | 17.5% in weight |
| $TiO_2$ | 15% in weight | $TiO_2$ | 17.5% in weight | b) Mingling

The constituents of each mixture are placed in a turbine mixer until perfect homogenising.

c) Drying

Each homogeneous mixture obtained is dried in an air circulation stove for 3 hours at 150° C.

d) Moulding

The moulding operation is performed on a KRAUSS-MAFFEL-type injection press. Model 90-340-32, KRAUSS MAFFEI FRANCE, 92632 GENNEVILLIERS—FRANCE.

The preparation conditions of the material and the moulding conditions of the mixture correspond to the commercial leaflet <<ICI MATERIALS>> specified above.

PEEK being a semi-crystalline thermoplastic, it is necessary to heat the mould to a temperature at least greater than that of its vitreous transition (140° C.). Failing which the surface quality of the moulded parts would be affected. Indeed, the surface web would be in amorphous phase and the core in crystalline phase; if the mould were too cold, the parts might even have totally amorphous character and the mechanical characteristics would drop considerably.

Thermoregulation of the mould is ensured by an oil reheater enabling to maintain it at a temperature of the order of 160° C. Insulation means limit thermal dispersions and preserve the peripheral organs of the injection press. Such means may be in the form of insulating plates formed of a fibre glass complex.

For series injections, a vibrator will be advantageously fixed to the hopper to promote the flow of the mixture.

Generally speaking, moulding is conducted at a temperature of the order of 340 to 400° C. and at an injection pressure close to 70 to 140 MPa.

The mould may be shaped in relation to the part to be obtained, for example for realising bone prosthesis, in particular for orthopaedic applications. A block of matter can also be obtained that will then be cut or machined to the desired shape, for bone filling or an implant, of dental type for example.

e) Surface Pickling—Decontamination

After obtaining the moulded material, the former is subjected to surface pickling and decontamination operations, before aseptic conditioning.

Such operations are conducted advantageously in a first step by passing the moulded material in different product baths subjected to ultrasounds; each product used may play the part of surface pickling agent or disinfectant, or both.

Obviously, the product(s) ensuring the surface pickling operation are suited, in combination with ultrasounds, to expose in surface in particular phosphorus and calcium (in the form of calcium phosphate), and titanium dioxide. Surface accessibility of the calcium phosphate promotes exchanges with the environment and electrostatic bonding of certain chemical elements present in the biological environment of the material after implantation, said exchanges and/or electrostatic bonding induce cellular penetration in the implanted material. Also, the presence of titanium dioxide in surface may induce said exchanges and the presence of electrostatic links.

Moreover, calcium phosphate being at least partially resorbable, its disappearance after implantation of the material enables to create cavities or a cavity network, promoting cellular penetration in the surrounding tissues.

The products used for these surface pickling and decontamination operations may be hydrochloric acid, (HCl, for example 30%) or sulphuric acid ($H_2SO_4$, for example 30%), acetone ($C_3H_6O$), hydrogen peroxide ($H_2O_2$, at 110 vol. or 30% for example), and/or sodium hypochlorite NaOCl used preferably in combination. Advantageously, complementary product baths are used with purely disinfecting function, such as Gigasept (registered trademark) or Lysetol (registered trademark).

The corresponding protocol for implementing these pickling/decontamination operations may consists in placing the implant in the different following successive baths subjected to ultrasounds:

HCl 30%: 20 mn
$H_2O$: 10 mn (or rinsing)
acetone: 20 mn
$H_2O$: 10 mn (or rinsing)
$H_2O_2$ 30%: 20 mn
NaOCl: 20 mn
$H_2O$: 10 mn (or rinsing)
Gigasept 12%: 60 mn
$H_2O$ Ppi: 20 mn (or rinsing)

The implant is inserted in a sterilisation sheath for passing in an autoclave; it is then subjected to a sterilisation cycle at a temperature of the order of 135° C. for 10 minutes, under a pressure of the order of 2150 mbars. This sterilisation operation by autoclave contributes to the surface pickling function; it may be associated with a treatment by ethylene oxide or by gamma rays.

f) Results

An electronic scanning microscope analysis shows that the pickling/decontamination and sterilisation operations promote the apparition of calcium phosphates in surface. These calcium phosphates emerge through micropores and crystallise.

After implantation, surface analysis shows the presence of holes and chaps at the surface of the material, and also the presence of carbon, oxygen and nitrogen, whereas little calcium and phosphorus can be found relative to the initial integrated concentrations.

This tends to show partial disappearance of the calcium phosphate particles in surface, and the colonisation of the holes and chaps by surrounding biological materials, sign of a graft-type biological acceptance.

Clinical analysis from inserted implants shows that the material in question develops at the contact thereof a cortical bone further to the physical and atomic characteristics of the material.

It is here a true graft principle; these results demonstrate the clinical reality of an integration of the material to the surrounding tissue.

The invention claimed is:

1. A method of preparation of a material for medical or veterinary usage, in order to ensure an efficient biocompatibility in terms of biological acceptance of said material which is in a form of a molded piecework ready for implantation into living bone tissue, comprising in specific order:
   injection molding the piecework from a material made of 65% to 90% in weight of a polymer biocompatible binder and 10% to 35% in weight of calcium phosphate;
   surface pickling and decontamination of the molded piecework, wherein said surface pickling and decontamination comprise passing the molded piecework in successive baths subjected to ultrasound in specific order:
   a hydrochloric or sulphuric acid bath,
   an acetone bath,
   a hydrogen peroxide bath,
   a sodium hypochlorite bath, and
   a disinfectant product(s),
   each of said baths being separated by operations comprising water rinsing or passing in water baths subjected to ultrasound; and
   a subsequent sterilization operation by autoclave,
   wherein said surface treatment is such as the surface of said molded piecework is provided with emerging crystallized calcium phosphate that is resorbable after implantation.

2. A method according to claim 1, which also comprises subjecting the molded part to a decontamination treatment by means of baths conducting the surface pickling/decontamination treatment, associated with at least one complementary bath of decontaminating product.

3. A method of preparation of a material for medical or veterinary usage, the material being in a form of a molded piecework ready for implantation into living bone tissue, made of a polymer biocompatible binder and at least one compound for adding calcium and phosphorus, comprising in specific order:
   mixing homogeneously 65% to 90% in weight of a polymer biocompatible binder and 10% to 35% in weight of calcium phosphate;
   subjecting the mixture thus obtained to a molding operation;
   performing, first, one or several surface pickling and decontamination operations on the molded piecework and, second, a sterilization operation by autoclave; and
   conditioning aseptically said decontaminated piecework,
   wherein the surface pickling and decontamination operations include passing the molded part in specific order in successive baths of hydrochloric or sulfuric acid, acetone, hydrogen peroxide, sodium hypochlorite and disinfectant product(s), subjected to ultrasounds, separated by operations consisting in water rinsing or passing in water baths subjected to ultrasounds, such as the surface of said molded piecework is provided with emerging crystallized calcium phosphate that is resorbable after implantation to insure an efficient biocompatibility in terms of biological acceptance.

4. A method according to claim 3, wherein the molding operation is an injection molding operation.

* * * * *